US00PP30958P3

(12) United States Plant Patent
Lindeman

(10) Patent No.: US PP30,958 P3
(45) Date of Patent: Oct. 22, 2019

(54) PEPPER PLANT NAMED 'RY5'

(50) Latin Name: *Capsicum annuum*
Varietal Denomination: RY5

(71) Applicant: Enza Zaden Beheer B.V., Enkhuizen (NL)

(72) Inventor: Wouter Lindeman, Woerden (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 0 days.

(21) Appl. No.: 15/732,242

(22) Filed: Oct. 11, 2017

(65) Prior Publication Data

US 2018/0042153 P1 Feb. 8, 2018

Related U.S. Application Data

(63) Continuation-in-part of application No. 15/493,000, filed on Apr. 20, 2017, which is a continuation-in-part of application No. 14/121,903, filed on Oct. 30, 2014, now Pat. No. Plant 28,123.

(60) Provisional application No. 62/366,927, filed on Jul. 26, 2016, provisional application No. 62/326,619, filed on Apr. 22, 2016, provisional application No. 61/899,010, filed on Nov. 1, 2013.

(51) Int. Cl.
*A01H 5/08* (2018.01)
*A01H 6/82* (2018.01)

(52) U.S. Cl.
USPC ..... Plt./258
CPC ..... *A01H 5/08* (2013.01); *A01H 6/822* (2018.05)

(58) Field of Classification Search
USPC ..... Plt./258, 263.1
CPC ..... A01H 6/822; A01H 5/08
See application file for complete search history.

(56) References Cited

U.S. PATENT DOCUMENTS

| | | | |
|---|---|---|---|
| PP28,123 | P3 | 6/2017 | Van et al. |
| 2015/0128320 | P1 | 5/2015 | Lindeman et al. |
| 2017/0223915 | A1 | 8/2017 | Lindeman et al. |
| 2018/0035590 | P1 | 2/2018 | Lindeman et al. |

OTHER PUBLICATIONS

Wouter et al., "Pepper plant named E20B3752", Unpublished U.S. Appl. No. 15/732,241, filed Jul. 24, 2017.
Wouter et al., "Pepper plant named YY5", Unpublished U.S. Appl. No. 15/732,241, filed Oct. 11, 2017.

*Primary Examiner* — Keith O. Robinson
(74) *Attorney, Agent, or Firm* — Morrison & Foerster LLP

(57) ABSTRACT

A new and distinctive variety of pepper (*Capsicum annuum*) plant named 'RY5' that is distinguished by its red and yellow striped colored and square shaped fruit.

2 Drawing Sheets

Latin name: Botanical classification: *Capsicum annuum.*
Varietal denomination: The varietal denomination of the claimed pepper variety is 'RY5'.

BACKGROUND OF THE INVENTION

The bell pepper (*Capsicum annuum*) originated in Mexico and the neighboring areas of Central America. Today, pepper plants can be found growing wild in tropical areas around the world. Soon after Columbus's discovery of this plant, it was grown worldwide and used as a spice and a medicine. Pepper is grown as a crop in many countries; hot peppers are generally grown in Latin America and China, while the United States prefers bell peppers. Peppers are used for both fresh consumption, and for processing into powders, sauces, and salsas. Many of the new cultivars grown today can be traced back to the early plants.

The genus *Capsicum* and species *annuum* includes most of the peppers grown in the United States. These can be further grouped into two broad categories: chile peppers which are pungent (hot) and sweet peppers which are non-pungent (mild). The United States produces four percent of the world's *capsicum* peppers (chile peppers and sweet peppers), ranking sixth behind China, Mexico, Turkey, Spain and Nigeria. Bell peppers are the most common sweet pepper and are found in virtually every retail produce department. While peppers are grown commercially in most states, the U.S. pepper industry is largely concentrated in California and Florida, which together accounted for 78% of output in 2000. New Jersey, Georgia, and North Carolina round out the top five producing states (Economic Research Service, USDA, Vegetables and Melons Outlook/VGS-288/Dec. 14, 2001).

Bell peppers are eaten raw, cooked, immature and mature. Often nutritional content is altered by the changes in the way they are consumed. Bell peppers are an excellent source of Vitamin C, Vitamin A, and Calcium. Mature red peppers have more of these qualities than the immature green peppers.

Peppers grown in temperate regions are herbaceous annuals, but are herbaceous perennials in regions where temperatures do not drop below freezing. Pepper plants' growth habit may be prostrate, compact, or erect, but it is determinate in that after it produces nine to eleven leaves a single stem terminates in flowers. These flowers then become the edible fleshy fruit for which these plants are grown. For fruit to set, the ovaries need to be fertilized. Auxin is then produced by the seeds, which determine fruit cell elongation. The number of seeds fertilized determines the size and shape of the fruit. The seeds develop on the interior and attach to the veins, and fully developed seed is kidney shaped. Pepper fruits are non-climacteric, which means they do not produce ethylene and need to stay on the vine to continue the ripening process. A deep taproot will form if the plant root system is uninjured during transplanting. The spindle root will develop fibrous secondary root systems spreading laterally and downward. On the soil surface the stem will produce adventitious roots, but not as easily as tomatoes. The leaves of the pepper plant arise singly and are simple, entire, and asymmetrical. Typical of all solanaceous plants, the leaves are arranged alternately on the stem. They are shiny and glabrous and vary in shape from broadly ovate to ovate lanceolate. The flowers develop singly or in twos or threes continuously as the upper structure of the plant proliferates. The corolla is white and five lobed while the anthers are bluish or yellowish in color. The flowers have an open anther formation and will indefinitely self-pollinate. They are also pollinated by insects, which increases the chances of cross-pollination. Unlike tomatoes, whose pollen becomes nonviable in high temperatures, the pepper flowers' pollen is not extremely heat sensitive and it remains viable up to 100° Fahrenheit, allowing fruit to be produced fruit throughout the growing season.

The fruit of a pepper plant is classified as a berry with colors including green, yellow, red, purple, black, brown, white, and orange. Pepper fruit developmental stages are characterized by their colors. Green is the color of an immature fruit, yet green peppers are commonly eaten, and as the fruit matures it changes color. In most commercial cultivars, the color changes are from green to red, green to yellow, or green to orange. In contrast to other pepper varieties, fruits of the purple and white varieties already have these colors as they develop, and therefore do not have a green stage.

Pepper is an important and valuable field crop. Thus, there is a continued need for new pepper varieties that are appealing to consumers and agronomically sound.

In order to meet these needs, the present invention is directed to a new pepper (*Capsicum annuum*) plant variety named 'RY5'. This new pepper plant variety is distinguished by its dark yellow and red striped color and square shape.

'RY5' was originally identified as a naturally occurring mutant in a screening trial of plants of pepper variety 'Healey' (not patented), conducted in Ontario, Canada in 2016. The mutant 'RY5' was selected based on its vertical red and yellow striped color and propagated vegetatively (i.e., asexually).

Subsequent screening trials of naturally occurring mutants of pepper variety 'Healey' conducted in Ontario, Canada and Michigan, United States identified further 'RY5' peppers. All 'RY5' peppers exhibit the vertical red and yellow striped color. When 'RY5' is propagated vegetatively via stem cuttings, the majority of offspring plants produce peppers that exhibit the vertical red and yellow striped color of 'RY5', with a low percentage of offspring plants producing peppers that exhibit a yellow color ('YY5', U.S. Plant patent application Ser. No. 15/732,241). Genetically, all 'RY5' peppers appear to have the same mutation. Without wishing to be bound by theory, it is believed that it is a genetic sensitivity in 'Healey' that gives rise to the 'RY5' mutant exhibiting the vertical red and yellow striped color.

The pepper plant variety 'RY5' has been asexually reproduced by stem cuttings at a farm in Ontario, Canada. Pepper plant variety 'RY5' is distinguished from all existing pepper plant varieties by the red and yellow striped fruit of the variety. The distinctive characteristics of pepper plant variety 'RY5' have been found to be stable and are transmitted to new pepper plants when asexually propagated.

In addition to the exemplary aspects and embodiments described above, further aspects and embodiments will become apparent by reference by study of the following descriptions.

SUMMARY OF THE INVENTION

The new pepper plant variety 'RY5' was selected for the red and yellow striped color and square shape of its fruit. Pepper plant variety 'RY5' is distinguished from the parental pepper plant variety 'Healey' in that the color of fruit of 'RY5' has vertical red and yellow stripes, while the fruit of 'Healey' is solid red in color.

Pepper plant variety 'RY5' is distinguished from striped pepper plant variety 'E20B3751' (U.S. Plant Pat. No. 28,123) in that 'RY5' produces leaves with an ovate shape that have a rounded base shape, while 'E20B3751' produces leaves with an elliptic shape that have an acute base shape. Additionally, flower buds of 'RY5' have a balloon shape, while flower buds of 'E20B3751' have a roundish to rectangular shape.

Pepper plant variety 'RY5' is distinguished from striped pepper plant variety 'E20B3752' (U.S. Plant patent application Ser. No. 15/731,725) in that 'RY5' produces mature fruit with a more smooth/less hammered fruit wall texture, while 'E20B3752' produces mature fruit with a less smooth/more hammered fruit wall texture. Additionally, 'RY5' plant architecture is more spreading, while 'E20B3752' plant architecture is more compact.

BRIEF DESCRIPTION OF THE DRAWINGS

This new pepper plant is illustrated by the accompanying photographs, which show fruit of the plant. The colors shown are as true as can be reasonably obtained by conventional photographic procedures.

FIG. 1A shows a side/bottom view of a ripe yellow and red striped fruit of hybrid pepper plant 'RY5'.

FIG. 1B shows a side view of two ripe yellow and red striped fruits of hybrid pepper plant 'RY5', as well as an unripe green fruit.

FIG. 1C shows a side view of two ripe yellow and red striped fruits of hybrid pepper plant 'RY5', as well as two unripe green fruits.

DETAILED DESCRIPTION OF THE INVENTION

Figure 1B:
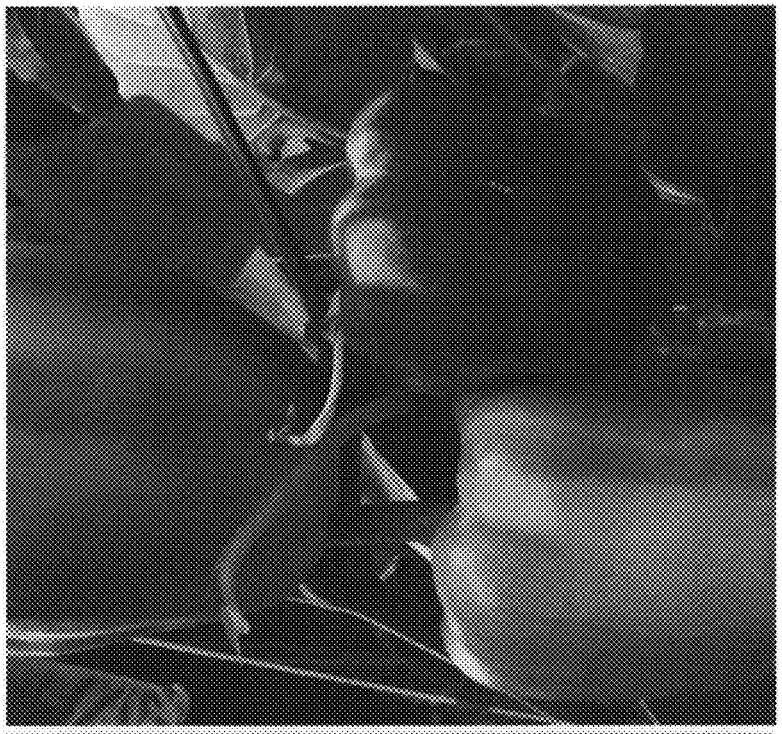
FIG. 1A-1C show several ripe yellow and red striped fruits of hybrid pepper plant 'RY5', as well as unripe green fruit.
Figure 1A:
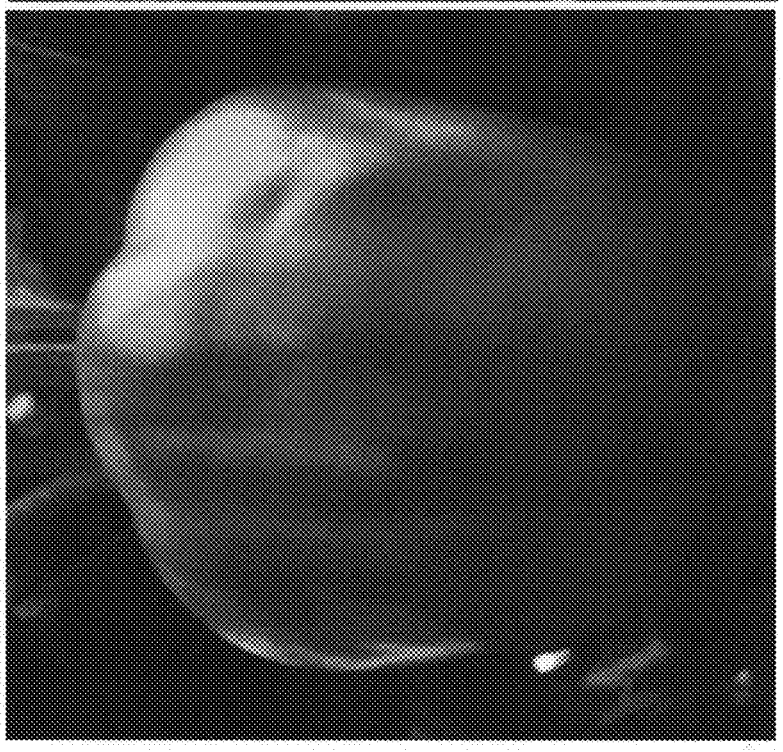
Figure 1C:
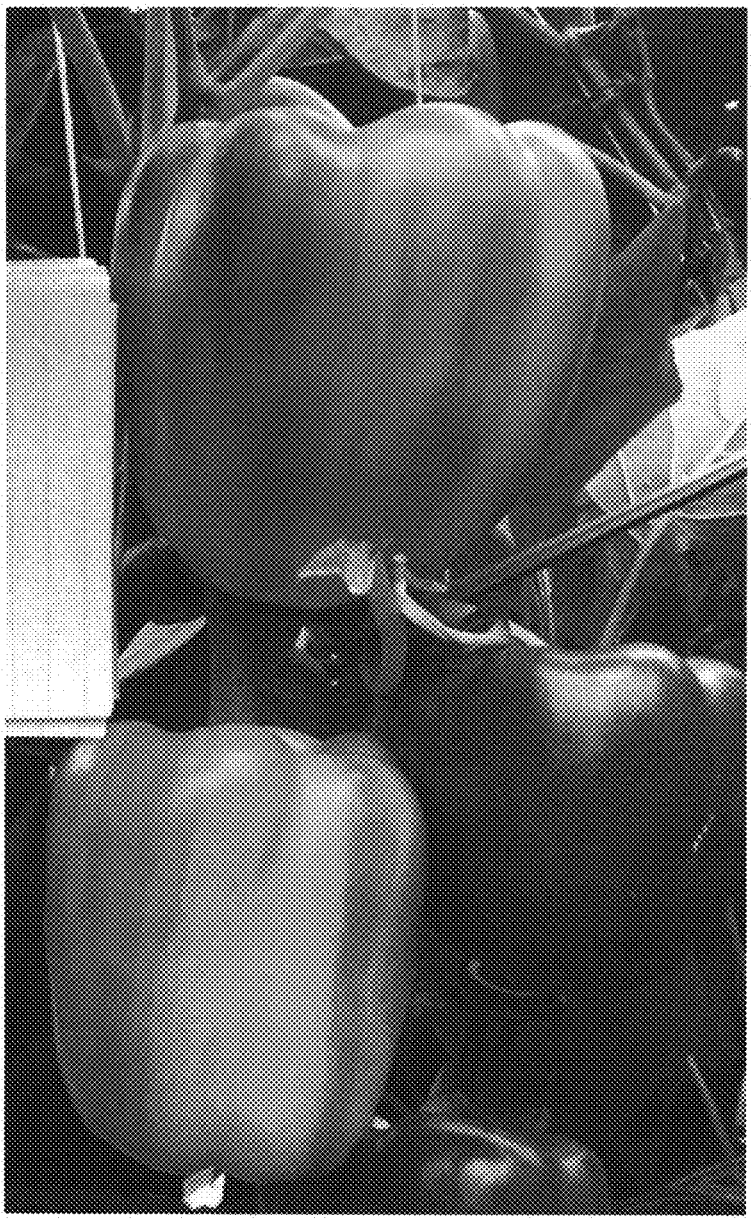

The following detailed descriptions set forth the distinctive characteristics of fruit grown from plants vegetatively propagated from the original mutant 'RY5' pepper plant. The data which define these characteristics, in particular the numerical values, are based on observations taken in a high-tech greenhouse in Enkhuizen, Netherlands in Autumn 2018. Numerical values, color designations and descriptions, and other phenotypical descriptions may deviate from the stated values and descriptions depending upon variation in environmental, seasonal, climatic, and cultural conditions. The following characteristics were observed on plants +/−4 months after rooting. The numerical values provided are representative values measured from these plants. 'RY5' has not been observed under all possible environmental conditions. Color references are primarily to The R.H.S. Colour Chart of The Royal Horticultural Society of London (R.H.S.) (2007 edition). Descriptive terminology follows the *Plant Identification Terminology, An Illustrated Glossary,* 2nd edition by James G. Harris and Melinda Woolf Harris, unless where otherwise defined.

Hybrid pepper plant variety 'RY5' has the following morphologic and other characteristics:

General:

*Usage*.—Fresh market.

*Type of culture*.—Covered cultivation (e.g., in greenhouse).

Plant:

*Stem diameter*.—1 cm.

*Shortened internode*.—Absent.

*Internode length*.—6 cm.

*Anthocyanin coloration of nodes*.—Present.

*Intensity of anthocyanin coloration of nodes on stem*.—Medium to strong.

*Hairiness of nodes on stem*.—Medium.

*Petiole length*.—6 cm.

*Petiole diameter*.—0.5 cm.

*Color of petiole*.—RHS 136A.

*Leaf shape*.—Ovate.

*Leaf shape of apex*.—Pointed.

*Leaf shape of base*.—Rounded.

*Leaf shape of margin*.—Slightly wrinkled.

*Undulation of leaf margin*.—Weak.

*Leaf blistering*.—Medium to strong.

*Leaf profile in cross section*.—Moderately convex.

*Leaf vein color*.—RHS 136A and RHS 137C.

*Leaf venation pattern*.—Pinnate.

*Leaf glossiness*.—Medium to strong.

*Leaf texture (upper and lower surfaces)*.—Smooth, slightly wrinkled.

*Leaf length of blade*.—20 cm.

*Leaf width of blade*.—13 cm.

*Intensity of green color of leaf blade*.—Medium to dark.

*Color of upper leaf surface*.—RHS 136A.

*Color of lower leaf surface*.—RHS 137C.

Flower:

*Flower bud length*.—1 cm.

*Flower bud diameter*.—0.5 cm.

*Flower bud shape*.—Balloon.

*Color of flower bud*.—RHS N999D.

*Flower diameter*.—3 cm.

*Flower depth*.—1 cm.

*Average number of petals per flower*.—6.

*Petal color (upper and lower surfaces)*.—RHS N999D.

*Petal length*.—1.5 cm.

*Petal width*.—0.5 cm.

*Petal shape of apex*.—Pointed.

*Petal margin*.—Smooth.

*Petal texture (upper and lower surfaces)*.—Smooth.

*Pistil length*.—0.5 cm.

*Stigma size*.—0.1 cm.

*Stigma shape*.—Rounded.

*Color of stigma*.—RHS 4A.

*Color of style*.—RHS N999D.

*Color of ovary*.—RHS 149A.

*Anther size*.—0.3 cm×0.1 cm.

*Anther shape*.—Linear.

*Anthocyanin coloration in anther*.—Present.

*Color of anther*.—RHS 96A and RHS 2C.

*Amount of pollen*.—Abundant.

*Time of beginning of flowering*.—Cuttings are taken from the generative part of the plants, so flowers are present from the beginning; plant flowers at transplant stage.

Fruit:

*Color before maturity*.—Green (RHS 137C).

*Intensity of color before maturity*.—Medium.

*Anthocyanin coloration before maturity*.—Absent.

*Attitude*.—Drooping.

*Shape in longitudinal section*.—Square.

*Shape in cross section (at level of placenta)*.—Angular to circular.

*Sinuation of pericarp at basal part*.—Absent or very weak.

*Sinuation of pericarp excluding basal part*.—Absent or very weak.

*Color at maturity*.—Red (RHS 45A) and yellow (RHS 23A) striped.

*Time of fruit maturity*.—Seven weeks after flowering.

*Number of locules*.—Equally three and four.

*Capsaicin in placenta*.—Absent.

*Fruit length*.—9.5 cm.

*Fruit width*.—8.5 cm.

*Ratio of length to diameter*.—1.12.

*Weight of fruit*.—180 to 220 grams.

*Texture of surface of fruit*.—Smooth or very slightly wrinkled.

*Glossiness of fruit*.—Medium.

*Stalk cavity*.—Present.

*Depth of stalk cavity*.—0.7 cm.

*Stalk length*.—6 cm.

*Stalk thickness*.—1 cm.

*Color of stalk*.—RHS 139C.

*Calyx aspect*.—Non-enveloping.

*Shape of apex of fruit*.—Moderately depressed.

*Depth of interloculary grooves*.—0.1 to 0.5 cm.

*Thickness of fruit flesh*.—0.8 cm.

*Seed length*.—0.4 cm.

*Seed width*.—0.4 cm.

*Color of seed*.—RHS 158A.

*Average number of seed per fruit*.—150 to 200.

*Fruit yield*.—20 to 25 kg/m2 when grown in a heated greenhouse.

Disease/pest resistance:

*Tobamovirus (tomato mosaic virus, tobacco mosaic virus, tobacco mild green mosaic virus, and pepper mild mottle virus) pathotype* $P_0$.—Resistant.

*Tobamovirus (tomato mosaic virus, tobacco mosaic virus, tobacco mild green mosaic virus, and pepper mild mottle virus) pathotype* $P_{1\text{-}2}$.—Resistant.

*Tobamovirus (tomato mosaic virus, tobacco mosaic virus, tobacco mild green mosaic virus, and pepper mild mottle virus) pathotype* $P_{1\text{-}2\text{-}3}$.—Susceptible.

*Tobamovirus (tomato mosaic virus, tobacco mosaic virus, tobacco mild green mosaic virus, and pepper mild mottle virus) pathotype* $P_1$.—Resistant.

*Potato virus Y pathotype* $P_0$.—Susceptible.

COMPARISON WITH PARENTAL AND RELATED KNOWN VARIETIES

Table 1 below compares the characteristic of the mutant pepper variety 'RY5' with the parental variety, 'Healey'. Column 1 lists the characteristic, column 2 shows the characteristics for mutant pepper variety 'RY5', and column 3 shows the characteristics for parental pepper variety 'Healey'.

TABLE 1

| Characteristic | 'RY5' | 'Healey' |
|---|---|---|
| Mature fruit color | Red (RHS 45A) and yellow (RHS 23A) striped | Red |

'RY5' differs from the striped pepper variety 'E20B3751' (U.S. Plant Pat. No. 28,123) in that leaves of 'RY5' have an ovate shape and a rounded base shape, while leaves of 'E20B3751' have an elliptic shape and an acute base shape. Additionally, flower buds of 'RY5' have a balloon shape, while flower buds of 'E20B3751' have a roundish to rectangular shape. Moreover, fruit of 'RY5' have dark yellow (RHS 23A) colored stripes at maturity, while fruit of 'E20B3751' have light yellow (RHS 14A) colored stripes at maturity.

'RY5' differs from the striped pepper variety 'E20B3752' (U.S. Plant patent application Ser. No. 15/731,725) in that plant architecture of 'RY5' is more spreading, while plant architecture of 'E20B3752' is more compact. Further, fruit of 'RY5' have a wall texture that is more smooth/less hammered, while fruit of 'E20B3752' have a wall texture that is less smooth/more hammered. Additionally, leaves of 'RY5' have an ovate shape, while leaves of 'E20B3752' have an elliptic shape. Moreover, flower buds of 'RY5' have a balloon shape, while flower buds of 'E20B3752' have a rectangular shape.

What is claimed:

1. A new and distinct pepper plant variety named 'RY5', as herein shown and described.

* * * * *